United States Patent [19]

Liu et al.

[11] Patent Number: 5,183,946

[45] Date of Patent: Feb. 2, 1993

[54] VINYLOXY HYDROXYALKYLCYCLOALKANE AND PREPARATION THEREFOR

[75] Inventors: Kou-Chang Liu, Wayne; Paul D. Taylor, West Milford, both of N.J.

[73] Assignee: ISP Investments Inc., Wilmington, Del.

[21] Appl. No.: 852,421

[22] Filed: Mar. 16, 1992

Related U.S. Application Data

[60] Continuation-in-part of Ser. No. 371,168, Jun. 26, 1989, abandoned, which is a division of Ser. No. 307,457, Feb. 8, 1989, abandoned.

[51] Int. Cl.$^5$ .............................................. C07C 41/00
[52] U.S. Cl. ...................................................... 568/670
[58] Field of Search ........................................ 568/670

[56] References Cited

U.S. PATENT DOCUMENTS 4,775,732 10/1988 Lapin ..................................... 560/44

Primary Examiner—Michael L. Shippen
Attorney, Agent, or Firm—Marilyn J. Maue; Joshua J. Ward

[57] ABSTRACT

The invention relates to a vinyloxy hydroxyalkyl cycloalkylene having the formula $$HO(CH_2)_x-A-(CH_2)_{x'}OCH=CH_2$$

wherein x has a value of from 1 to 10; x' has a value of from 0 to 10 and A is a cycloalkylene group having from 3 to 8 carbon atoms in the ring and is optionally substituted with lower alkyl. The invention also relates to the method for synthesizing the above compounds.

10 Claims, No Drawings

VINYLOXY HYDROXYALKYLCYCLOALKANE AND PREPARATION THEREFOR

CROSS-REFERENCE TO RELATED PATENT APPLICATIONS

This application is a continuation-in-part of Ser. No. 371,168, filed Jun. 26, 1989, now abandoned, which is a division of application Ser. No. 307,457, filed Feb. 8, 1989 (now abandoned).

BACKGROUND OF THE INVENTION

This invention relates to compounds having a vinyl group and a hydroxyl group as terminal groups of the compound. More particularly, this invention relates to monomers which possess a vinyl ether substituent and a hydroxyl substituent.

Urethane polymers have had great commercial success when used as protective coatings, films and adhesives. The genesis for these polymers is usually a monomer having both an acrylic functional group and a hydroxyl functional group. In the process for making a protective coating or film the hydroxyl group is converted to a urethane group by reaction with an isocyanate. The resulting acrylic urethane monomer is then applied to a surface and cured thereon by radiation. However, this process for producing urethane coatings and films has many shortcomings.

Since the polymerization and curing of acrylic functional groups proceeds by a free radical mechanism, polymerization and curing must be carried out in the absence of air, a known free radical inhibitor. The oxygen free atmosphere can be achieved by effecting the polymerization under a blanket of nitrogen; however this requirement greatly increases the cost of the process.

Another disadvantage in the preparation of acrylic urethane coatings is that a curing rate sufficiently high to meet certain requirements such as coatings for automotive fascia, etc., are not achievable by radiation exposure. Finally, it is found that urethane coatings made from acrylic urethane monomers have poor adhesion to hard, smooth surfaces such as metal or glass.

It is therefore an object of this invention to provide a compound which can be converted to a urethane monomer having a high radiation cure rate in the absence or presence of air to produce a coating of excellent adherence to hard surfaces such as glass or metal.

Another object is to provide an economical and commercially feasible process for the manufacture of the present compounds.

Still another object is to provide a substrate coated with the present compound which possesses superior stability.

These and other objects of the invention will become apparent from the following description and disclosure.

THE INVENTION

In accordance with this invention, there is provided a vinyloxy hydroxyalkyl cycloalkane compound having the structure

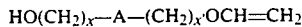

wherein x has a value of from 1 to 10; x' has a value of from 0 to 10 and A is a cycloalkylene group having from 3 to 8 carbon atoms in the ring and is optionally substituted with lower alkyl. Preferred of this group are those compounds wherein x and x' each have a value of from 1 to 4 and, most preferably, where A is cyclohexylene.

The compounds of this invention are useful chemical intermediates. For example, these products can be polymerized to branched structures having repeating units of

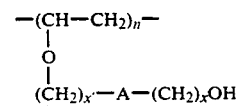

The polymer chains in turn, can be cross-linked at the terminal hydroxy group by condensation, by dehydration or by reaction with polyols, such as diols, to form the corresponding ethers. Additionally, they can be reacted with diacids, both aliphatic and aromatic dicarboxylic acids, to form the corresponding esters. These polymers, because of branching and/or cross-linking provide coatings which are more resistant to chemical attack and abrasion than linear types and are adapted to curing by irradiation at a reasonably high rate. Also, the polymers provide a harder more durable surface on the substrate after curing than the linear polymerized products. A major advantage of the present products is their ability to be converted to vinyl ether urethanes by reaction with an isocyanate, e.g. according to the equation:

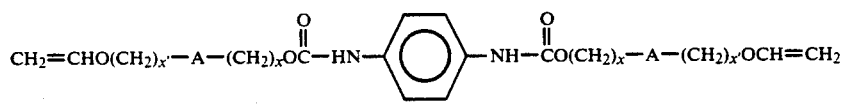

These urethanes polymerize and are rapidly cured by a cationic mechanism activated by radiation, e.g. from UV light or an electron beam source, to form hard, durable coatings; thus eliminating the need for formation under a blanket of nitrogen which is required by free radical polymerization and curing.

It is readily apparent that the present compounds can also be employed as monomers in copolymerizations with other monomers selected from the groups consisting of olefinic compounds, maleic anhydride, vinyl pyrrolidone, acrylics, methacrylics, etc. The products in their non-polymerized state are also useful in the formation of many non-polymeric compounds through condensation, dehydration, esterification, substitution at the hydroxy site or addition to the terminal vinyl group; thus providing useful multifunctional reaction intermediates.

The present products are readily synthesized by reacting a diol corresponding to the formula

with acetylene. Examples of suitable diols include 1,4-di(hydroxymethyl) cyclohexane; 1,5-di(hydroxydecyl) cyclooctane; 1,3-di(hydroxyethyl) ethylcyclopentane; 4(4-hydroxycyclohexyl) butanol; (3-hydroxy)-2,5-dimethyl-cyclooctyl decanol; etc. In this reaction the mole ratio of diol to acetylene can vary between about 1:1 and about 1:1.5. At low reaction pressure, the acetylene can be introduced into the reaction zone without dilution; however, at elevated pressures, it is recommended that an inert non-oxygen containing gaseous diluent such as nitrogen, a $C_1$-$C_3$ alkane or helium be used to dilute the acetylene reactant. When the diluent is employed, acetylene concentration as low as 10% can be used although between about 40 and about 60 wt. % acetylene in diluent is most preferred.

The above reaction is carried out in an oxygen free atmosphere which is generally achieved by purging with nitrogen and is effected in the presence of a basic catalyst such as an alkali metal hydroxide, e.g. potassium hydroxide, or sodium hydroxide as potassium alkoxide or an amine. The concentration of catalyst employed can range from about 0.1% to about 5% by weight.

The process is effected at a temperature of between about 120° C. and about 200° C. under from about 10 to about 200 psig. in a period of from about 2 to about 20 hours reaction time. Preferred conditions include a temperature of between about 140° C. and about 170° C., under between about 50 and about 100 psig. for a period of from about 4 to about 8 hours. The present process shows a significant selectivity to the desired monovinyl ether product over the divinyl ether by-product, particularly when carried out over a period of from 2 to 6 hours.

Having thus generally described the invention, reference is now had to the following examples which illustrate preferred embodiments but which are not to be construed as limiting to the scope of the invention as more broadly set forth above and in the appended claims.

EXAMPLE I

Molten 1,4-bis-(hydroxymethyl) cyclohexane (1802.6 grams) and 36 grams of potassium hydroxide pellets (85%) were charged with a one gallon autoclave. The autoclave was purged three times with nitrogen, then evacuated to 10 mm of mercury pressure and heated at 90° C. for 30 minutes to remove water of reaction.

Propane gas was introduced into the autoclave to 60 psi and the autoclave heated to 160° C. Additional propane gas was added at 160° C. until the pressure reached 100 psi. Acetylene was then introduced until a total pressure of 200 psi was achieved. After 6.5 hours at 200 psi and 160° C. the autoclave was cooled to room temperature, purged 3 times with nitrogen, and its contents discharged.

The crude product (1,816 g.) was distilled under vacuum (1 mm Hg) using a 15 plate Oldershaw column, and a clear water white fraction boiling between 95° C. and 110° C. was collected. The fraction boiling at 102° C. weighed 263 grams and was identified as 99.3% pure monovinyl ether of 1,4-bis-hydroxymethyl cyclohexane by nmr, using $CD\ Cl_3$ solvent.

EXAMPLE II

Example 1 was repeated except that 1,5-bis-(hydroxyethyl) cyclooctane is substituted for 1,4-bis-(hydroxymethyl) cyclohexane. The divinyl ether product is recovered in greater than 90% yield.

EXAMPLE III

After pulling a vacuum for 30 minutes at 90° C. to remove water, 1802.6 g. of 1,4-cyclohexane dimethanol was contacted with 650 g. of acetylene in propane diluent in the presence of 36 g. of 85% potassium hydroxide (KOH). The reaction was carried out at 160° C. and 100 psig acetylene and 100 psig propane. Aliquots of the product mixture were taken at time intervals and analyzed by gas chromatography. These results are shown in the following Table and the reaction product containing

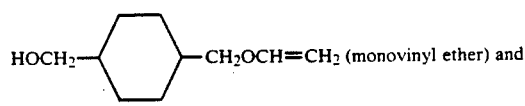

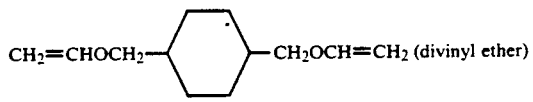

by-product was recovered.

TABLE

| Reaction Time | Diether | Mono Ether cis | Mono Ether trans | Diol |
|---|---|---|---|---|
| 2 | 1.87 | 9.2 | 3.2 | 62.6 |
| 3 | 9.6 | 29.5 | 10.3 | 37.7 |
| 4 | 14.1 | 33.4 | 11.4 | 30.5 |
| 5 | 27.67 | 36.5 | 11.9 | 17.6 |
| 6 | 32.0 | 36.7 | 11.8 | 14.3 |
| 6.5 | 40.0 | 34.6 | 10.9 | 16.4 |

EXAMPLE IV

The above reaction was repeated except that the temperature employed was 175° C. Substantially the same selectivity to the monovinyl ether was observed.

What is claimed is:

1. A method of synthesizing the compound

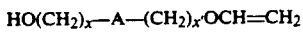

wherein x has a value of from 1 to 10; x' has a value of from 0 to 10 and A is a cycloalkylene group having from 3 to 8 carbon atoms in the ring and is optionally substituted with lower alkyl, which comprises reacting a diol having the structure

wherein x, x' and A are as defined with acetylene in an inert diluent in an oxygen free atmosphere at a temperature of from about 120° C. and about 200° C. under a pressure of from about 10 psig. to about 200 psig. and recovering the product of the process.

2. The method of claim 1 wherein the reaction is effected under a pressure of from about 20 psig. to about 100 psig. and the acetylene is diluted with an inert gas.

3. The method of claim 2 wherein the concentration of acetylene in said gas is between about 10% and about 60% by weight.

4. The method of claim 2 wherein said gas is selected from the group of nitrogen, a $C_1$ to $C_3$ alkane helium.

5. The method of claim 4 wherein said gas is propane.

6. The method of claim 2 wherein acetylene is diluted to a concentration of between about 40% and about 60% by weight.

7. The method of claim 1 wherein said reaction is effected at a temperature of between about 140° C. and about 170° C. under from about 50 psig. to about 100 psig. in the presence of a basic catalyst.

8. The process of claim 7 wherein said catalyst is an alkali metal hydroxide.

9. The process of claim 2 wherein said diol is bis(hydroxymethyl) cyclohexane.

10. The process of claim 1 wherein said reaction is carried out over a period of from about 2 to about 6 hours.

* * * * *